(12) United States Patent
Baldwin

(10) Patent No.: US 10,087,526 B2
(45) Date of Patent: Oct. 2, 2018

(54) STENTS, PACKAGING, AND SUBSTANCES USED WITH STENTS

(71) Applicant: MicroVention, Inc., Tustin, CA (US)

(72) Inventor: Aaron Baldwin, Orange, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 532 days.

(21) Appl. No.: 14/575,229

(22) Filed: Dec. 18, 2014

(65) Prior Publication Data

US 2015/0173919 A1    Jun. 25, 2015

Related U.S. Application Data

(60) Provisional application No. 61/919,659, filed on Dec. 20, 2013.

(51) Int. Cl.
| | |
|---|---|
| *C23C 16/513* | (2006.01) |
| *A61F 2/00* | (2006.01) |
| *A61F 2/90* | (2013.01) |
| *A61L 31/08* | (2006.01) |
| *A61L 31/14* | (2006.01) |
| *C23C 16/50* | (2006.01) |
| *A61F 2/95* | (2013.01) |

(52) U.S. Cl.
CPC .......... *C23C 16/513* (2013.01); *A61F 2/0095* (2013.01); *A61F 2/90* (2013.01); *A61L 31/08* (2013.01); *A61L 31/14* (2013.01); *C23C 16/50* (2013.01); *A61F 2002/9522* (2013.01); *A61F 2230/0021* (2013.01); *A61F 2230/0056* (2013.01); *A61F 2240/001* (2013.01); *A61F 2250/0096* (2013.01); *A61F 2250/0098* (2013.01); *Y10T 29/49863* (2015.01)

(58) Field of Classification Search
CPC ... B32B 15/04; A61N 1/05; A61F 2/02; A61F 2/0095; A61F 2/90; C23C 16/513; C23C 16/50; A61L 31/08; A61L 31/14
USPC ............... 424/423; 427/2.24, 536, 537, 539; 607/120; 428/450
See application file for complete search history.

(56) References Cited

U.S. PATENT DOCUMENTS

| | | | |
|---|---|---|---|
| 2002/0009604 A1* | 1/2002 | Zamora | A61L 29/08 428/450 |
| 2007/0141104 A1* | 6/2007 | Hauenstein | A61L 29/10 424/423 |
| 2008/0234792 A1* | 9/2008 | Reddy | A61N 1/057 607/120 |

* cited by examiner

*Primary Examiner* — Dah-Wei D Yuan
*Assistant Examiner* — Andrew Bowman
(74) *Attorney, Agent, or Firm* — Inskeep IP Group, Inc.

(57) ABSTRACT

Polymers have many positive properties which make them beneficial as a material used in a vascular—and neurovascular—implant, such as a stent. Stents comprising polymers, methods of making stents comprising polymers, packaging for stents, and adhesives, coatings and other materials used on stents are described. Also described are stents with flared ends having bends.

24 Claims, 10 Drawing Sheets

STENTS, PACKAGING, AND SUBSTANCES USED WITH STENTS

RELATED APPLICATIONS

This application claims priority to U.S. Provisional Application Ser. No. 61/919,659 filed Dec. 20, 2013 entitled Stents, Packaging, And Substances Used With Stents, which is hereby incorporated herein by reference in its entirety.

BACKGROUND OF THE INVENTION

Stents may be used for a variety of purposes within the vasculature, such as providing a scaffold for therapeutic materials, reducing flow to a particular region of the vasculature, or restoring flow to a particular region of the vasculature. Polymers have many positive properties which make them beneficial as a material used in a vascular—and neurovascular—implant, such as a stent. Stents of particular designs, stents comprising polymers, methods of making stents comprising polymers, packaging for stents, and adhesives, coatings and other materials used on stents are described.

SUMMARY OF THE INVENTION

In one embodiment a stent comprising one or more polymers is described.

In another embodiment a stent comprising one or more polymers and one or more non-polymers is described.

In another embodiment a high-porosity stent comprising one or more polymers is described.

In another embodiment a low-porosity stent comprising one or more polymers is described.

In another embodiment a stent including post woven modification of the polymeric surface is described.

In another embodiment a single layer polymer stent is described.

In another embodiment a multiple layer polymer stent is described.

In another embodiment a single strand polymer stent is described.

In another embodiment a multiple strand polymer stent is described.

In another embodiment a method of manufacturing a polymer stent is described.

In another embodiment a stent flare is described.

In another embodiment a polymer stent comprising a stent flare is described.

In another embodiment a non-polymer stent comprising a stent flare is described.

In another embodiment a stent flare with a secondary bend is described.

In another embodiment a polymer stent comprising a stent flare with a secondary bend is described.

In another embodiment a non-polymer stent comprising a stent flare with a secondary bend is described.

In another embodiment a stent flare with a curved radius is described.

In another embodiment a polymer stent comprising a stent flare with a curved radius is described.

In another embodiment a non-polymer stent comprising a stent flare with a curved radius is described.

In another embodiment a stent flare with a curved radius and a secondary bend is described.

In another embodiment a polymer stent comprising a stent flare with a curved radius and a secondary bend is described.

In another embodiment a non-polymer stent comprising a stent flare with a curved radius and a secondary bend is described.

In another embodiment a stent packaging system is described.

In another embodiment a method of delivering a stent utilizing a stent packaging system is described.

In another embodiment an adhesive is described.

In another embodiment a stent marker utilizing an adhesive is described.

In another embodiment a method of applying an adhesive to a stent marker is described.

In another embodiment a stent is made of an adhesive material.

In another embodiment a process of coating a polymer stent is described.

In another embodiment a method of coating a polymer stent is described.

DESCRIPTION OF EMBODIMENTS

Figure 1:
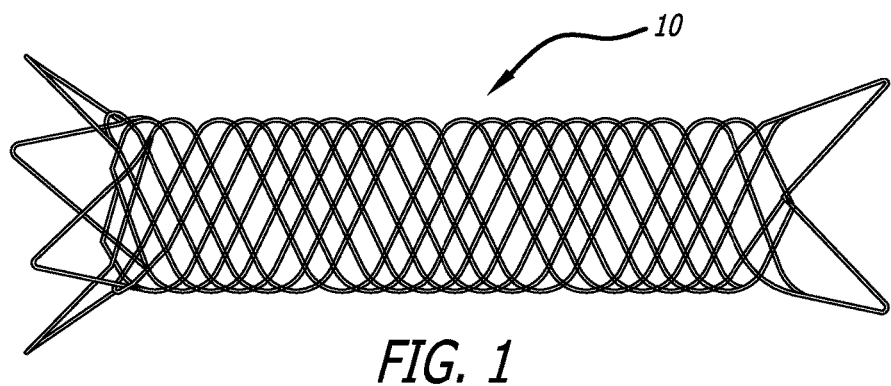
FIG. 1 illustrates a polymer stent.

The term 'polymer stent' as used herein may be used to describe a stent comprised entirely of one or more polymer materials as well as a stent comprising one or more polymer materials combined with one or more non-polymer (e.g., metallic, or other non-polymeric) materials.

Polymers have many properties which are advantageous for use in stents. Innate MRI compatibility, degradable properties, and ease of surface modification with a wide array of biologically active surface coatings and/or drugs are among these advantageous properties.

A woven stent may be composed of a polymeric drawn fiber of high elastic modulus. In one embodiment polyetheretherketone (PEEK) is used In another embodiment polysulfone (PS) is used. And in yet another embodiment polyethersulfone (PES) is used. In another embodiment various combinations of PEEK, PS, and PES are used (e.g.,. PEEK and PS, PS and PES, PEEK and PES, PEEK PS and PES).

A high elastic modulus material (elastic modulus being analogous to Young's modulus) is chosen to provide an inert and non-biodegradable scaffold of which minimal thrombus is formed in contact with body fluids. Materials with a high elastic modulus also tend to be stiffer thus retaining their shape better. Shape retention is a desirable property for a stent as stents can be used to keep constricted passageways open, or may be used as a scaffold through which other materials are placed (e.g., aneurysm embolic coils, where said stent acts as a bridge for the neck of the aneurysm). In other embodiments various polymers such as polyimides, polyarylethers, high elastic-modulus polymers, and combinations therein may be used.

In another embodiment, instead of being woven, a polymer stent can be composed of one or more of the polymers just described where said stent is a solid tube with notches or regions cut from said tube to create the gaps in the stent to allow blood flow or allow passage of therapeutic or interventional material such as embolic coils or other embolic material.

In another embodiment a stent comprising one or more polymers (e.g., the polymers specified earlier and combinations therein) and one or more non-polymers (e.g., nitinol, stainless steel, platinum, tantalum, cobalt-chromium, and combinations therein).

The polymeric drawn fiber may be on the order of 0.001" to 0.005" in diameter and can be woven such that it can be collapsed elastically into a smaller diameter catheter (e.g., one with an inner diameter of 0.017" to 0.038").

The radial force of the stent should be such that the struts oppose the wall sufficiently to prevent migration of the stent after deployment but without causing vessel damage. To that end the hoop force, or radial force, of the stent may be normalized per unit stent length to 0.5-2.5 gram-Force/mm. Stent radial force may be dependent on various factors such as winding tension, properties of the constituent polymeric fibers, stent porosity, etc. Porosity is a measure of the open area of the stent and can be defined as the ratio of the open area of the stent to the total surface area of the stent, or the ratio of the metal surface area of the stent to the total area of the stent subtracted from 100%.

In another embodiment the polymer stent made of the constituent materials described earlier may be woven with a relatively high porosity (e.g., >90%). A high porosity stent is useful, in one example, to provide access to an aneurysm where treatment devices (aneurysm embolic coils or polymeric glues) are placed through the open surfaces within the stent. A thinner material (e.g., smaller diameter of the constituent material), the winding pattern density (e.g., lower density vs. higher density), and the number of layers comprising the stent (e.g., one layer vs. two or more layers) are some variables that can affect the porosity of the stent.

In another embodiment the polymer stent made of the constituent materials described earlier may be woven with a relatively low porosity (e.g., <80%). A low porosity stent may be useful, in one example, as a flow diverter. The low porosity stent can be placed across the opening of an aneurysm diverting blood flow into the aneurysm to help reduce the chance of rupture and allow clotting to seal the aneurysm. A thicker material (e.g., larger diameter of the constituent material), the winding pattern density (e.g., higher density vs. lower density), and the number of layers comprising the stent (e.g., two or more layers vs. one layer) are some variables that can affect the porosity of the stent.

In another embodiment the polymer stent of the previous embodiments includes post woven modification of the polymeric surface to differentiate the biological response of the material. This can be accomplished, for example, by chemical modification of the surface via plasma treatment, covalent attachment or proteins, peptides, or other hydrophilic polymers.

In one embodiment the polymer stent is composed of a single drawn monofilament arranged in a single layer. In another embodiment the polymer stent is composed of a single monofilament arranged in multiple layers. This can be done by creating one layer, then reversing the winding to draw the monofilament back and create a second layer, etc.

In another embodiment the polymer stent is composed of multiple monofilaments arranged in a single layer. In another embodiment the polymer stent is composed of a monofilament comprising one or more materials (e.g., the monofilament may be made from a combination of materials wound into a single strand, or the monofilament may have a section comprising one material and another connected section comprising another material, etc). In another embodiment the polymer stent is composed of multiple monofilaments which are braided to create more than one layer.

The single-layer stent embodiments, in one example, would be more useful as high porosity stents (such as those used as scaffolds to insert therapeutic materials such as coils or polymeric glues). The multiple-layer stent embodiments, in one example, would be more useful as low porosity stents (such as flow diverting stents) where subsequent layers may decrease the overall porosity of the stent. The stents described may be wound on a mandrel (by hand, or via an automated winding machine), and heat-set to retain the final shape before being removed from the mandrel.

Figure 2:
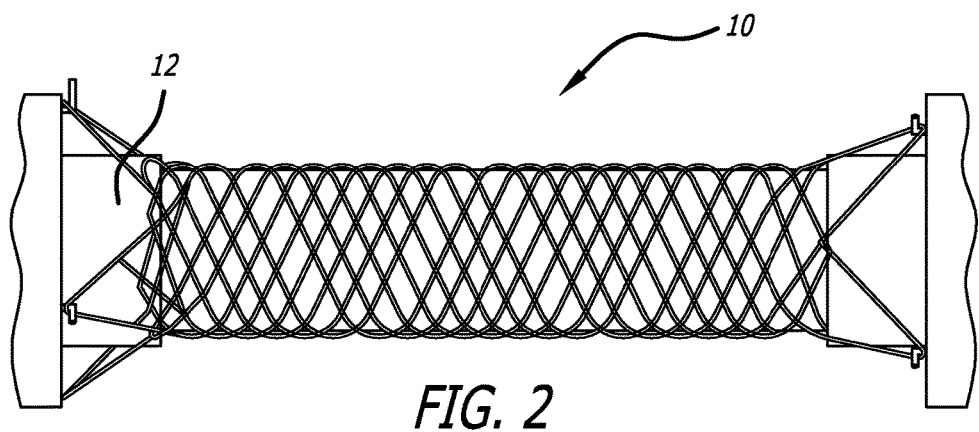
FIG. 2 illustrates a fixture used to wind a polymer stent.

FIG. 1 shows a woven polymer stent 10. FIG. 2 shows the mandrel 12 on which polymer stent 10 is wound.

Figure 3:
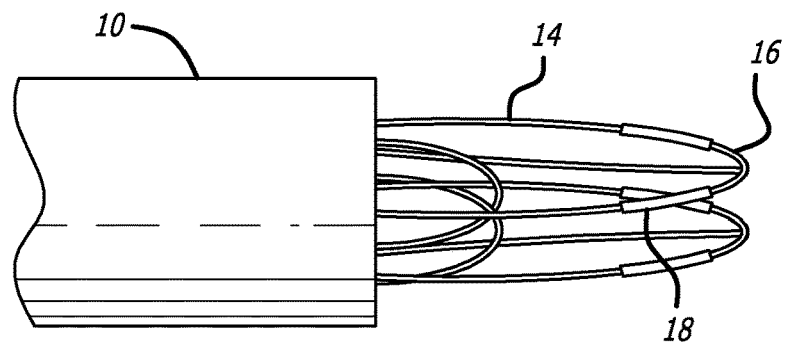
FIG. 3 illustrates a stent with non-flared end loops.

Stents typically contain loops at the proximal and distal end of the stents. FIG. 3 shows the end of a stent 10 through a catheter, where the stent end contains loops 14. The loops 14 may optionally include marker coils 18 and the loops have an end portion 16. The marker coils 18 are comprised of a radiopaque material (i.e. tantalum or platinum) and are useful for imaging of the device during delivery.

Figure 4:
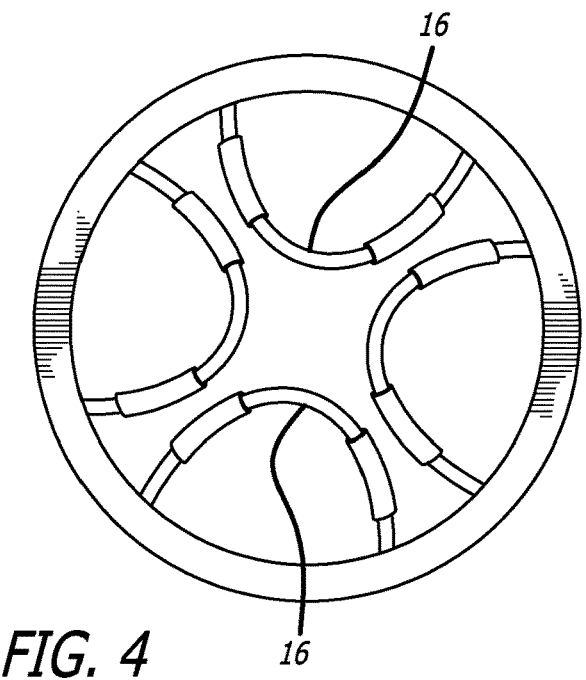
FIG. 4 illustrates the stent from FIG. 3 inside a delivery device.

Stent delivery through the microcatheter, catheter, or delivery device may be complicated due to a phenomenon known colloquially as fish-mouthing, where the ends of the loops are forced into the lumen of the stent when it is compressed down to a smaller diameter. This is shown in FIG. 4 where the loop ends 16 project inwards. This phenomenon may make it difficult for the stent to completely open up when the stent is pushed out from the delivery device.

Figure 5:
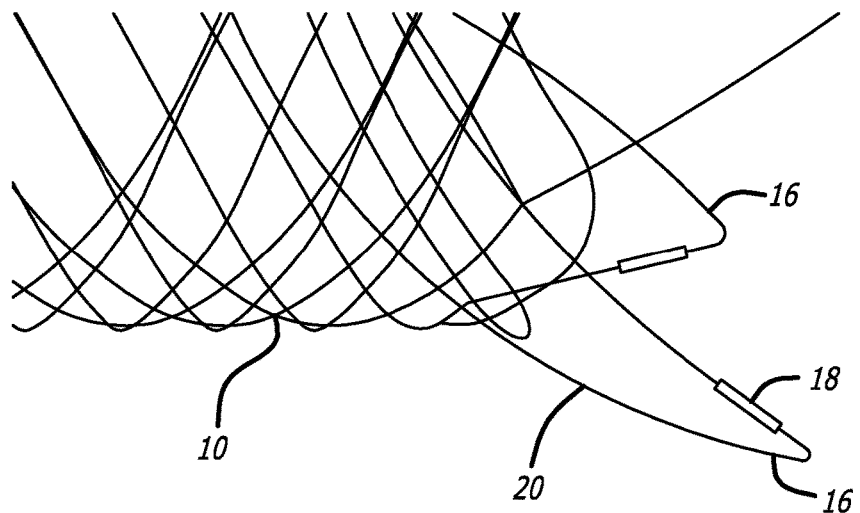
FIG. 5 illustrates a stent with flared end loops.

One potential solution to fish-mouthing is to add one or more flares 20 as shown in FIG. 5 to the end of the stent 10 to help prevent the ends from kinking inwards during delivery. The flares 20 extend out at a larger diameter than the rest of the stent 10. However, a bit of kink may still be present with the flares 20 when the stent 10 is sheathed which may still complicate stent delivery.

Figure 6:
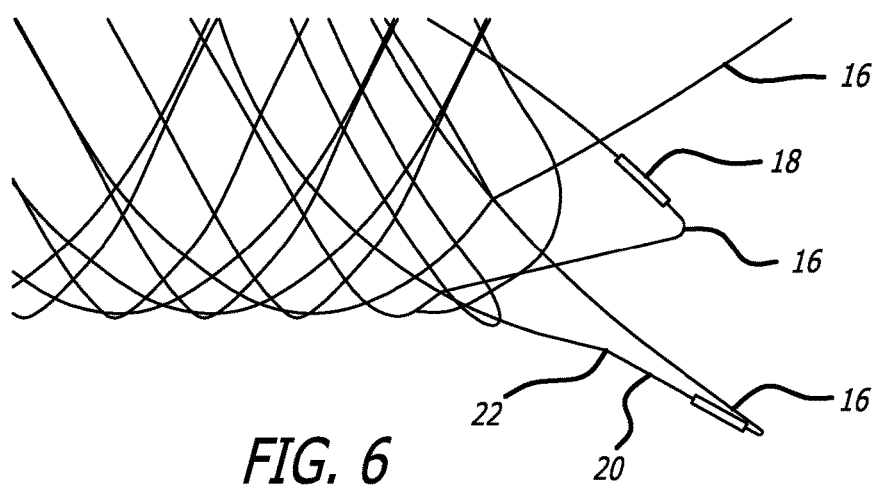
FIG. 6 illustrates a stent with flared end loops utilizing a secondary bend.
Figure 7:
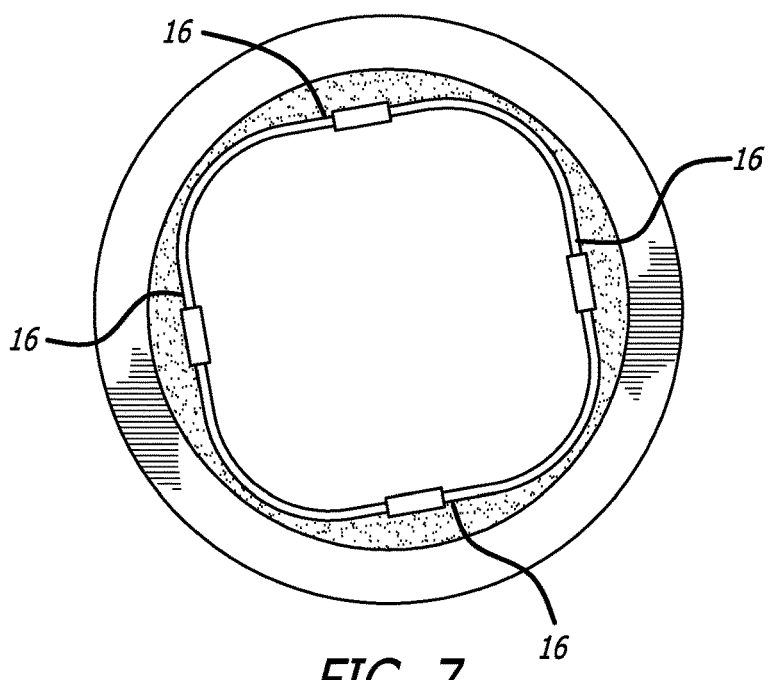
FIG. 7 illustrates the stent of FIG. 5 within a delivery device.
Figure 8:
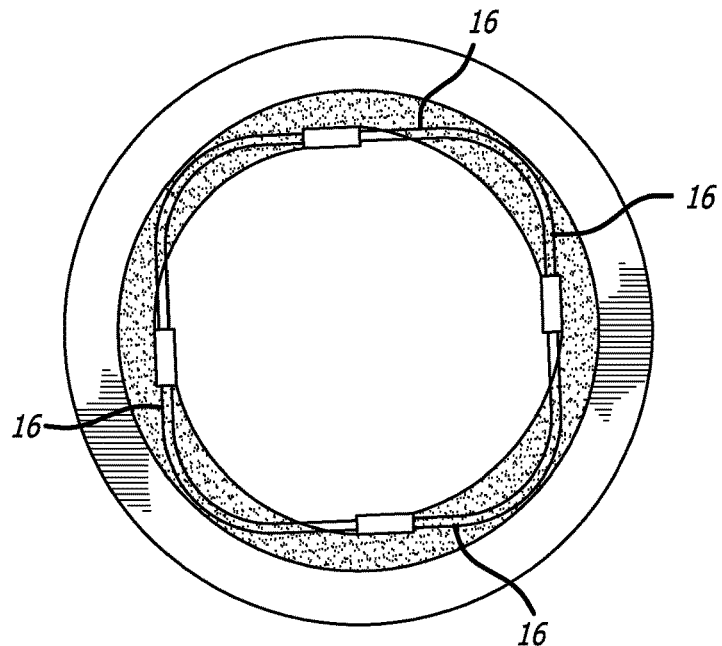
FIG. 8 illustrates the stent of FIG. 6 within a delivery device.

Another possible solution, as shown in FIG. 6, is to add one or more secondary bends 22 to the stent flares 20 so that as the stent 10 collapses there is an additional bend on the extending loop 14 away from the body of the stent 10. The secondary bend 22 can be designed to force the long loop out greatly or only a minor angle change such as what is shown in FIG. 6. The stents of FIGS. 5 and 6 are shown during delivery, respectively, in FIGS. 7 and 8. The stent 10 with the secondary bend 22 from FIG. 6 is shown in FIG. 8, and the stent 10 generally fills the periphery of the delivery device better, which will make stent delivery easier within the vasculature.

In another embodiment a polymer stent may utilize a flare 20 with a secondary bend 22. One or more secondary bends on one or more of the loops/flares may be used. Polymer stents may be more structurally rigid than traditional metallic stents (e.g. those comprised of nitinol, stainless steel, or cobalt-chromium), thus the inclusion of a flare 20 and secondary bend 22 will help the polymer stent 10 to fully open up during delivery. In another embodiment a stent 10 comprised of any material—including one or more polymers, or a non-polymeric material in combination with one or more polymers, or solely non-polymeric materials—may utilize a flare 20 with a secondary bend 22. In one example a crimping tool can be used to introduce the bend 22 into the flare 20. The crimping tool attaches to a portion of the flare 20 and stays on the flare 20 during the heat treatment procedure and is removed after the heat treatment to set the bend shape into the stent flare 20.

Figure 9A:
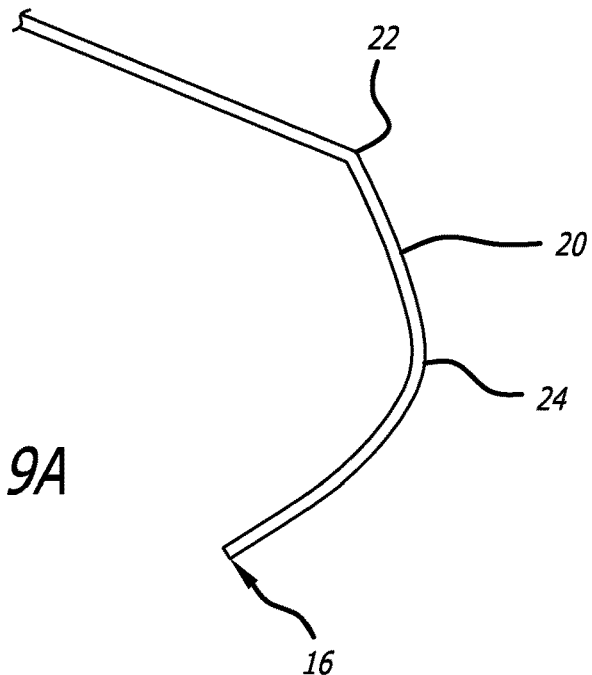
FIG. 9A illustrates a stent with both a secondary bend and a curved radius.
Figure 9:
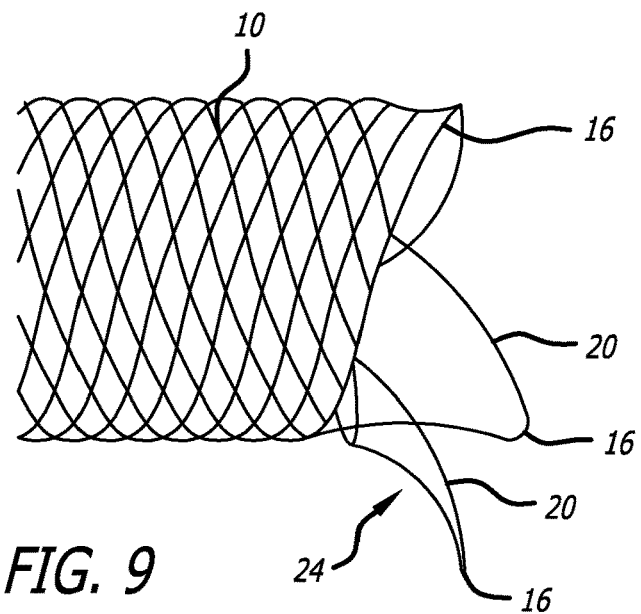
FIG. 9 illustrates a stent with flared end loops utilizing a curved radius.

Another embodiment shown in FIG. 9 could utilize a curved radius 24 instead of a bend 22 at the end of the stent flare 20. The entire end of the stent flare 20 could be bent to create a curved radius 24. The curved portion of the stent flare 20 would project outward against the delivery catheter, mitigating fish-mouthing and aiding in the full expansion of the stent during deployment. Polymer stents may be more structurally rigid than traditional metallic stents (e.g., those comprised of nitinol, stainless steel, or cobalt-chromium), thus the inclusion of a flare 20 and curved radius 24 will help the polymer stent to fully open up during delivery. In another embodiment a stent composed of any material—including one or more polymers or a non-polymeric material in combination with one or more polymers, or solely non-polymeric materials—may utilize a flare 20 with a curved radius 24. In one example a conformable sleeve with a curved radius shape is placed over the flare ends to promote the curved radius shape and the stent is subsequently heat set with said sleeve still on the flared end to set the shape. The sleeve is then removed after the heat treatment step.

Another embodiment could utilize both a curved radius 24 with a secondary bend 22 located somewhere along the curved radius as shown in FIG. 9A. This could be used on one, all, or some of the flares. Another embodiment could utilize a curved radius 24 along one or more of the stent flares 20, and one or more secondary bends 22 on one or more of the stent flares 20.

In another embodiment a polymer stent utilizes a curved radius 24 and a secondary bend 22 on one or more flares, wherein said curved radius 24 has a secondary bend 22 somewhere along said curved radius 24. In another embodiment a polymer stent utilizes a curved radius 24 on one or more flares 20, and a secondary bend 22 on one or more different flares 20. In another embodiment a non-polymer stent utilizes a curved radius 24 and a secondary bend 22 on one or more flares 20, wherein said curved radius 24 has a secondary bend 22 somewhere along said curved radius 24. In another embodiment a non-polymer stent utilizes a curved radius 24 on one or more flares 20, and a secondary bend 22 on one or more different flares 20.

Long term storage of polymer stents is difficult since polymeric materials such as thermoplastics cannot be stored over long periods of times (e.g., weeks to months) in a crimped state and remain self expanding at the time of use. In another embodiment a packaging system is described that can be used with stents, particularly polymer stents, but also non-polymeric stents.

Figure 10:
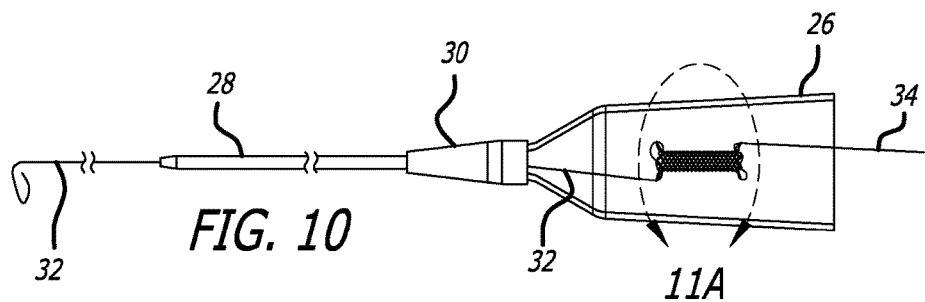
FIGS. 10-11 illustrate a stent packaging system.

Referring to FIG. 10, the stent can be stored in an expanded state within an introducing funnel 26. Please note for FIGS. 10 and 11 items on the left side are considered distal relative to items on the right side of the Figures.

Funnel 26 is connected to introducer 28 which has a strain relief section 30. The funnel 26 has a proximal larger diameter region in which the stent initially sits and a smaller diameter region at the distal part of the funnel 26 which connects to a smaller diameter strain relief section 30 of the introducer 28. The introducer 28 has the same inner diameter as the strain relief inner diameter. The strain relief external diameter is larger, as shown in FIG. 10, to promote material strength during handling by the user.

Figure 11:
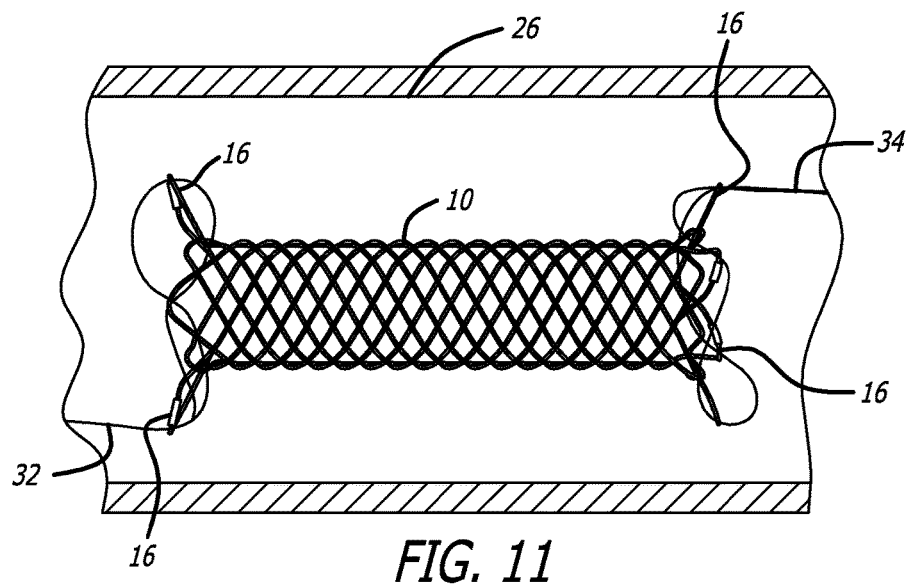

A purse string 32 may be wrapped around loops 16 at a distal end of stent 10 (see FIG. 11). The purse string 32 extends out through the distal end of introducer 28, as shown in FIG. 10. Another purse string 34 may optionally be wrapped around the loops 16 on the proximal end of the stent 10. The inclusion of this second purse string 34 would help keep the stent in a uniformly compressed state when the stent 10 is pulled through the funnel 26 and introducer 28 via the user pulling on purse string 32. The user would pull lightly on purse string 34 to ensure the stent 10 is in a fully compressed state as the stent 10 navigates through the funnel 26 and introducer 28.

The one or more purse strings may be made of a high tensile strength thermoplastic. Polyetheretherketone, polyester, polypropylene, or polyethylene, or various combinations of said materials may be used for the purse strings. Alternatively a metallic material or alloy may be used. In one example the purse strings are comprised of polyetheretherketone of a diameter of 0.002".

Purse string 32 is pulled and this pulling action causes the stent 10 to move through funnel 26 and introducer 28. If purse string 34 is included, the user can simultaneously pull lightly on purse string 34 to ensure the stent 10 is fully compressed during navigation through the funnel 26 and introducer 28. When stent 10 is near the distal end of introducer 28 purse string 32 can be cut (the majority, or all of purse string 32 being exposed once the stent is near the distal end of introducer 28). A cannula hub is then connected to the introducer 28 and funnel 26 is cut or removed.

A pusher is introduced through introducer 28 which is connected to stent 10 and used to push the stent 10 through the microcatheter/delivery device. The introducer 28 may be removed once the stent 10 is in the microcatheter/delivery device. The stent packaging system is comprised of stent 10, purse string 32 and optional purse string 34, funnel 26, and introducer 28.

In another embodiment, a method of delivering a stent utilizing a stent packaging system utilizes the steps described above.

The stent packaging system and method of delivering a stent utilizing a stent packaging system may utilize a polymeric or non-polymeric (i.e. metallic) stent, or a stent utilizing polymeric and non-polymeric elements.

Figure 12A:
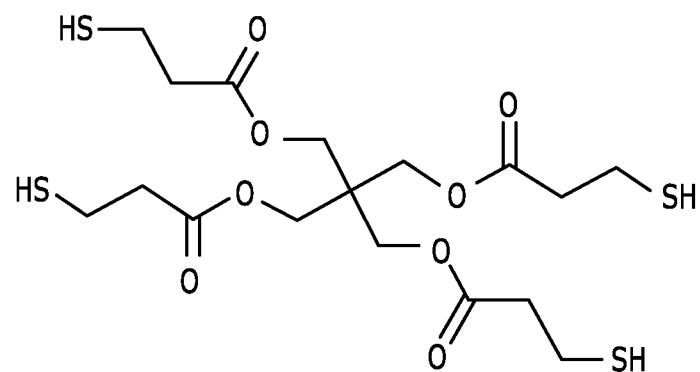
FIGS. 12A-12B, 13A-13E and 14 illustrate compounds used in an adhesive.
Figure 12B:
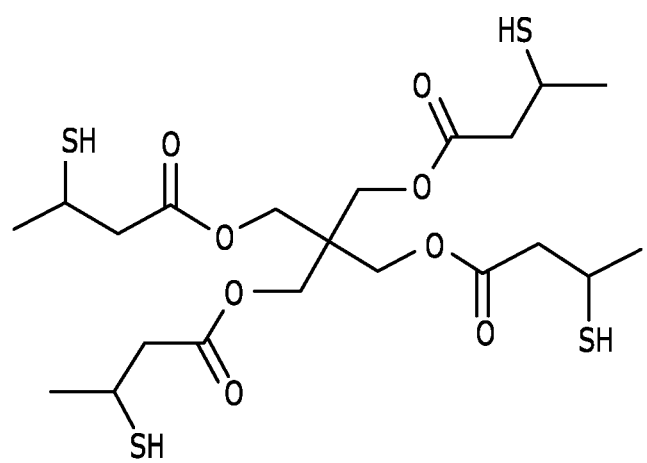
Figure 13A:
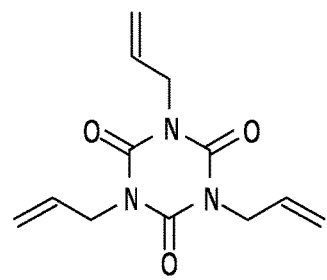
Figure 13B:
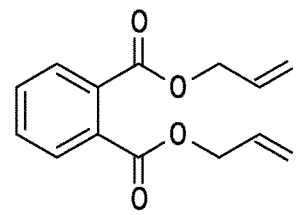
Figure 13C:
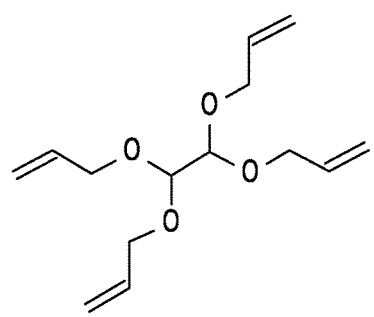
Figure 13D:
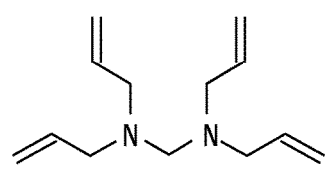
Figure 13E:
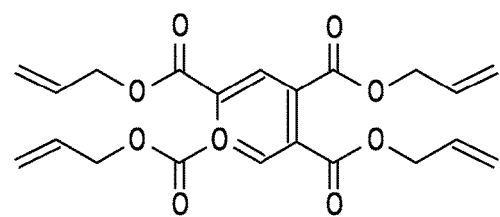
Figure 14:
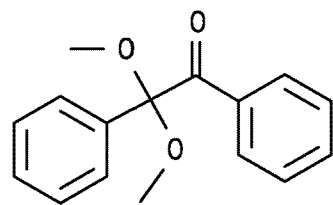

In another embodiment an adhesive is described. The adhesive may be used for a variety of reasons and on a variety of devices, including medical devices such as stents, occlusive coils, etc. A thiol-ene adhesive can be cured via UV light to subsequently encapsulate or glue parts of a medical device (e.g., stent). The UV glue comprises three components, including one or more thiol monomers (FIGS. 12A, 12B), one or more vinyl monomers (FIGS. 13A-13E), and typically one type of photo-initiator (FIG. 14). The UV glue can be comprised of various combinations of these three components. In one embodiment, the adhesive is composed of Pentaerythritol tetrakis (3-mercaptobutylate or PETMB from FIG. 12B), triallyl-1,3,5-triazine-2,4,6-trione (TTT from FIG. 13A), and 2,2-Dimethoxy-2-phenylacetophenone (DMPA from FIG. 14). Subsequent embodiments can utilize various combinations of the compounds shown in FIGS. 12A, 12B, 13A-13E, and 14. Other thiol monomers, vinyl monomers, and photo-initiators beyond the ones shown may also be used.

In another embodiment the adhesive described above can be used with a marker coil on a stent, where said stent can be polymeric, non-polymeric, or contain polymeric and non-polymeric elements. Marker coils are radiopaque coils (i.e. made of tantalum, platinum, or other radiopaque material) placed at the ends of a stent to aid in visualization of the stent during deployment and placement within the vasculature. The use of an adhesive (such as the one described earlier) would help to augment the retention strength of the coil to the stent.

Figure 15:
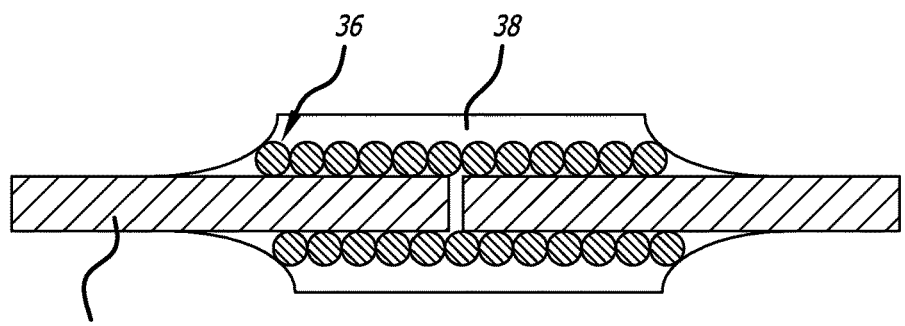
FIG. 15 illustrates a marker coil configuration utilizing an adhesive.

In one embodiment, marker coils 36 are wound around a polymer fiber 34 (see FIG. 15). Alternatively, a marker 36 is pre-wound on a mandrel and the polymer is loaded into the coil. A polymer fiber 34 is described just for purposes of example. A metal (e.g., nitinol, stainless steel, cobalt-chromium, combinations therein) or combination metal-polymer can also be used. For better bond strength of the adhesive to the polymer, the polymer can be plasma treated to increase adherence, but this is not necessary. Adhesive 38 is then applied over coil 36 and set using UV light (wavelength range of about 200 to about 600 nanometers). In another embodiment the steps described above can be used with any adhesive, including the adhesive embodiments described above. In another embodiment a method of encapsulating a marker utilizes the steps described above and shown in FIG. 15.

In another embodiment the thiol-ene adhesive previously described may be used in a stent. In one example the whole stent is composed of this adhesive material. In another example the stent is composed of this adhesive material along with at least one other material (i.e. metallic, polymeric, or combinations therein).

In another embodiment a process of coating a polymer stent is described.

A common issue with coating of medical devices, including stents, is the adhesion to the substrate material. Poor adhesion leads to surface defects and reduced coating performance. Phosphorylcholine is often used as a medical device coating. Phosphorylcholine is a zwitterionic head group of a lipid bilayer present in high concentration of the exterior of red blood cells, thus using this functional group on the surface of materials mimics a natural biologic surface. Mimicry of naturally occurring surfaces has been shown to reduce the amount of denatured proteins deposited on foreign surfaces and thereby increase the blood compatibility of the coated material.

In the first step of the process, a functionalized surface must be imparted to the surface to allow for covalent attachment of the molecules to the surface. Covalent attachment guaranties a permanently attached functional layer of high durability for subsequent reactions. A plasma polymerization technique can be used to functionalize the surface with thiol groups (—SH). A plasma chamber (i.e. PVA Tepla's ION 40 fitted with a vapor phase mass flow controller) is used as part of the plasma polymerization.

Figure 16:
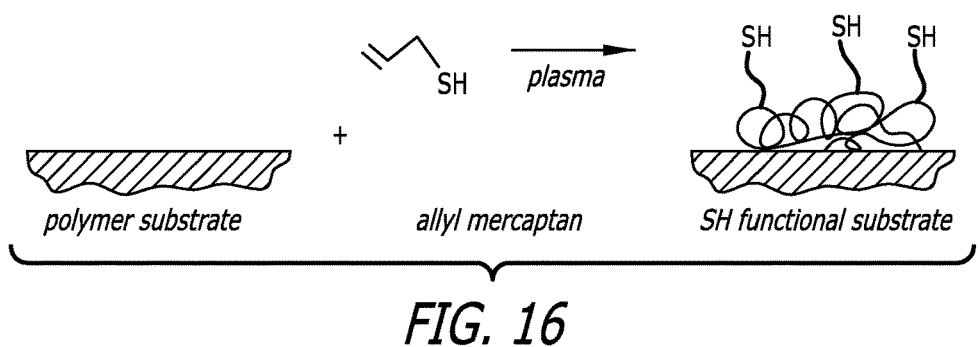
FIGS. 16-18 illustrate steps used in a coating process.

Initially the polymer substrate is cleaned with a brief oxygen plasma treatment in the plasma chamber. The oxygen is then vacuumed out of said chamber. Subsequently the plasma chamber is charged with allyl mercaptan. See Journal of Adhesion Science and Technology 2002, 16, 1529-1543 which is hereby incorporated by reference in its entirety. The high energy polymerization would covalently deposit a polymer with thiols on the surface (see FIG. 16).

Figure 17:
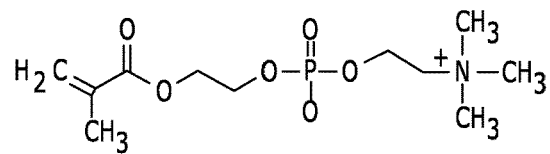
Figure 18:
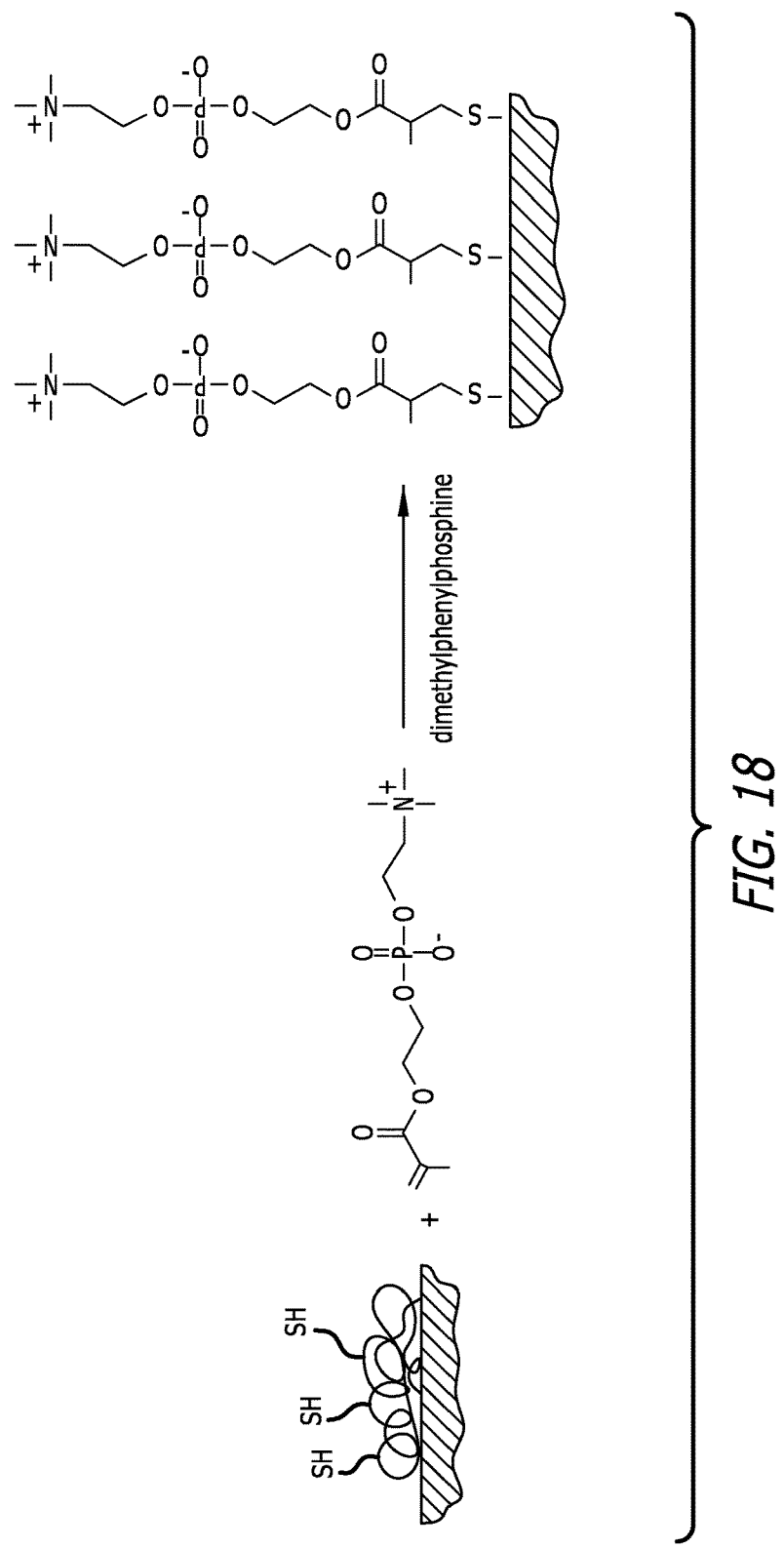

In the second step of the process, phosphorylcholine must be added to the functionalized surface created in the first step. Phosphorylcholine is readily available in a methacrylated form (see FIG. 17). Methacrylates are not typically used with Michael addition chemistries. Dimethylphenylphosphine may be used as a catalyst to enable addition reactions between thiols and methacrylates, see Polym. Chem. 2010, 1, 1196-1204 which is hereby incorporated by reference in its entirety. FIG. 18 displays the reaction scheme for the addition of 2-Methacryloyloxyethyl phosphorylcholine to the surface functionalized thiols of FIG. 16.

In another embodiment a method of coating a polymer stent utilizes the steps just detailed.

The polymer stents described may utilize other coatings, such as drug-eluting coatings to create a drug-eluting polymer stent.

What is claimed is:

1. A method of coating a stent comprising:
   placing a stent within a plasma chamber;
   introducing oxygen into said plasma chamber;
   purging said oxygen from said plasma chamber;
   charging the plasma chamber with allyl mercaptan; and
   exposing the stent to a methacrylated phosphorylcholine in the presence of a phosphine catalyst.

2. The method of coating a stent of claim 1 wherein exposing the stent to the methacrylated phosphorylcholine in the presence of the phosphine catalyst comprises exposing the stent to 2-methacryloyloxyethyl phosphorylcholine.

3. The method of coating a stent of claim 1 wherein exposing the stent to the methacrylated phosphorylcholine in the presence of the phosphine catalyst comprises exposing the stent to dimethylphenylphosphine.

4. The method of coating a stent of claim 1 wherein placing a stent within a plasma chamber comprises placing a polymeric stent in the plasma chamber.

5. A method of coating a stent comprising:
   imparting a functionalized surface on a stent; and
   covalently bonding a hydrophilic polar head group to the functionalized surface of the stent in the presence of a phosphine catalyst.

6. The method of coating a stent of claim 5 wherein imparting the functionalized surface on the stent comprises plasma polymerization.

7. The method of coating a stent of claim 5 wherein imparting the functionalized surface on the stent comprises covalently depositing a nucleophilic group on the stent surface.

8. The method of coating a stent of claim 5 wherein imparting the functionalized surface on the stent comprises covalently depositing a polymer having a thiol.

9. The method of coating a stent of claim 5 wherein imparting the functionalized surface on the stent comprises treating the stent with allyl mercaptan.

10. The method of coating a stent of claim 5 wherein covalently bonding the hydrophilic polar head group to the functionalized surface of the stent in the presence of a phosphine catalyst comprises covalently bonding a phosphorylcholine head group to the functionalized surface of the stent.

11. The method of coating a stent of claim 5 wherein covalently bonding the hydrophilic polar head group to the functionalized surface of the stent in the presence of a phosphine catalyst comprises covalently bonding 2-methacryloyloxyethyl phosphorylcholine to the functionalized surface of the stent.

12. The method of coating a stent of claim 5 wherein covalently bonding the hydrophilic polar head group to the functionalized surface of the stent in the presence of a phosphine catalyst comprises covalently bonding a hydrophilic polar head group to the functionalized surface of the stent in the presence of a dimethylphenylphosphine.

13. The method of coating a stent of claim 5 further comprising cleaning the stent with an oxygen plasma treatment.

14. The method of coating a stent of claim 5 wherein the stent is polymeric.

15. A method of coating a stent comprising:
covalently depositing a first monomer on the stent surface, wherein the first monomer comprises:

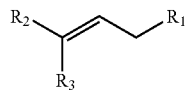

wherein $R_1$ is a nucleophilic group, and $R_2$ and $R_3$ are a hydrogen;
reacting a second monomer and a catalyst with the first monomer deposited on the stent surface, wherein the second monomer comprises:

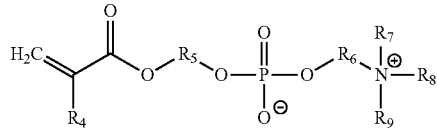

wherein $R_4$ is an alkane, $R_5$ is $C_1$-$C_2$, $R_6$ is $C_1$-$C_2$, and $R_7$, $R_8$, and $R_9$ are a methyl; wherein the nucleophilic group of the first monomer forms covalent bonds with a terminal —$CH_2$ group of the second monomer through an addition reaction.

16. The method of claim 15 wherein the first monomer comprises allyl mercaptan.

17. The method of claim 15 wherein $R_1$ of the first monomer comprises a thiol group.

18. The method of claim 15 wherein covalently depositing a first monomer on the stent surface comprises plasma polymerization.

19. The method of claim 15 wherein the second monomer comprises a phosphorylcholine.

20. The method of claim 15 wherein the second monomer comprises an electrophilic methacrylate moiety.

21. The method of claim 15 wherein the catalyst comprises a phosphine, a primary amine or a tertiary amine.

22. The method of claim 15 wherein the phosphine catalyst is a dimethyl phenylphosphine.

23. The method of claim 15 wherein the addition reaction is a Michael addition.

24. The method of coating a stent of claim 15 further comprising cleaning the stent with an oxygen plasma treatment.

* * * * *